(12) United States Patent
Diaconu et al.

(10) Patent No.: US 11,096,571 B2
(45) Date of Patent: Aug. 24, 2021

(54) ANOMALOSCOPE HAVING PIXELS EMITTING MONOCHROMATIC LIGHT AT THREE WAVELENGTHS

(71) Applicants: Vasile Diaconu, Notre-Dame-de-l'Ile-Perrot (CA); Jean-Marie Hanssens, La Prairie (CA); Marc Melillo, Danville (CA)

(72) Inventors: Vasile Diaconu, Notre-Dame-de-l'Ile-Perrot (CA); Jean-Marie Hanssens, La Prairie (CA); Marc Melillo, Danville (CA)

( * ) Notice: Subject to any disclaimer, the term of this patent is extended or adjusted under 35 U.S.C. 154(b) by 107 days.

(21) Appl. No.: 16/493,375

(22) PCT Filed: Mar. 19, 2018

(86) PCT No.: PCT/CA2018/050331
§ 371 (c)(1),
(2) Date: Sep. 12, 2019

(87) PCT Pub. No.: WO2018/170588
PCT Pub. Date: Sep. 27, 2018

(65) Prior Publication Data
US 2020/0029804 A1 Jan. 30, 2020

Related U.S. Application Data

(60) Provisional application No. 62/474,261, filed on Mar. 21, 2017.

(51) Int. Cl.
*A61B 3/06* (2006.01)
*A61B 3/00* (2006.01)
(52) U.S. Cl.
CPC ............ *A61B 3/066* (2013.01); *A61B 3/0033* (2013.01)

(58) Field of Classification Search
CPC .............................. A61B 3/066; A61B 3/0033
(Continued)

(56) References Cited

U.S. PATENT DOCUMENTS 4,765,731 A * 8/1988 Williams ............... A61B 3/066
351/242
5,609,159 A * 3/1997 Kandel ............... A61B 3/1176
351/221
(Continued)

FOREIGN PATENT DOCUMENTS

GB 2411010 A 8/2005

OTHER PUBLICATIONS

International Search Report of PCT/CA2018/050331; dated May 28, 2018; Laila Khalid.

*Primary Examiner* — Collin X Beatty
(74) *Attorney, Agent, or Firm* — BCF LLP

(57) ABSTRACT

An anomaloscope comprises a display and a controller of the display. The display has pixels arranged in a plurality of groups, each group containing at least three pixels, each pixel being capable of emitting monochromatic light at a distinct wavelength. The controller of the display causes the display to emit, in at least one of the plurality of groups, light at a first wavelength and causes the display to emit, in at least another one of the plurality of groups, light at two other wavelengths. The controller of the display controls intensities of the light emitted at each of the distinct wavelengths to generate of a pair of metameric colors between the light emitted at the first wavelength and a combination of the light emitted at the two other wavelengths. A method uses the anomaloscope to assess an ability of a subject to discriminate between colors.

25 Claims, 6 Drawing Sheets

(58) Field of Classification Search
USPC .......................................................... 351/222
See application file for complete search history.

(56) References Cited

U.S. PATENT DOCUMENTS

| | | | | |
|---|---|---|---|---|
| 5,908,394 | A * | 6/1999 | Kandel | ................ A61B 3/1173 |
| | | | | 600/558 |
| 10,912,457 | B2 * | 2/2021 | Schmeder | ................ A61H 5/00 |
| 2005/0105796 | A1 * | 5/2005 | Hong | ........................ G09G 5/02 |
| | | | | 382/162 |

* cited by examiner

ANOMALOSCOPE HAVING PIXELS EMITTING MONOCHROMATIC LIGHT AT THREE WAVELENGTHS

TECHNICAL FIELD

The present disclosure relates to the medical fields of optometry and ophthalmology. More specifically, the present disclosure relates to an anomaloscope having pixels emitting monochromatic light at three wavelengths.

BACKGROUND

All theories that have attempted to explain the vision of the colors in primates are founded on the discovery, by Newton in the 17$^{th}$ century, relative to the dispersion of white light.

The Newton discovery suggests that white light is composed of several elementary color components, each component of the white light generating a typical colorful feel. The white sensation would be the result of a simultaneous excitation by all the color components constituting the white light.

One century later, Thomas Young demonstrated that the white sensation can alternatively be obtained from a simultaneous excitation of three colored lights, including red, green and blue.

Furthermore, Thomas Young demonstrated that the color sensation, specific to a given elementary colored light, could be created by a mixture of selected other elementary colored lights. As a result, Thomas Young introduced the concept of "metameric colors". Two colored lights are considered metameric, when the perceptual appearances of these lights are identical while their spectral compositions are different.

However, it has been demonstrated that, by way of a mixture of the three fundamental colors red, green, and blue, in various intensities, it is possible to reproduce all colorful sensations engendered by the colored elements constituting the white light.

From this illusory phenomenon, the idea that the colorful sensation arises from the excitement of the three photoreceptors types of the retina with a specific sensitivity, relatively to the various colored components of the white light, has been advanced.

In fact, the colorful sensation is expressed at the level of the brain, following a perceptive process activated by a light excitation on the three cells types in the eye, called cones. The colorful sensation is a subjective process and so, it would be specific to each individual who expresses it.

At the beginning of the 17$^{th}$ century, Turberville reported that some individuals can present a distinctive perception for the colors. The method used by Turberville to name the colors was subjective, but may be regarded as the first method which has emphasized individual colors' perception differences.

In 1881, Lord Rayleigh invented the anomaloscope, an instrument based on physical and perceptual strong principles and governed by the Rayleigh equation, known as «Rayleigh Match». A mixture of red and green monochromatic lights (usually of 670 nm and respectively of 535 nm) applied on a half of the circular surface is to be matched with the monochromatic yellow light (usually of 589 nm) applied on the other half of the circular surface. The psycho-physical procedure on the anomaloscope consists in adjusting the intensity of the monochromatic yellow light by the subject, in an attempt to find a correspondence with various mixtures of the red and green lights. The subject's ability to differentiate colors is evaluated from all the mixtures of red and green lights, designated by the subject as identical with a specific intensity of the yellow monochromatic light.

Employing the anomaloscope, Rayleigh has identified and categorized the anomalies in human color vision regarding the perception of red and green lights. Dichromacy is characterized by the lack of one of red or green cone types. Abnormal trichromacy, which is less severe, occurs when one or both of red and green cone types present abnormal spectral sensitivity.

On a similar principle as the Rayleigh match, some anomaloscopes employ the Moreland match to test the perceptive dysfunctions for the blue light.

In accordance with the Moreland proposal, a mixture of blue and green monochromatic lights (usually at 440 nm and 588 nm, respectively) is matched with a cyan monochromatic light (usually of 470 nm). The cyan monochromatic light appears saturated comparatively to all blue and green light mixtures. For that reason, Moreland has proposed to desaturate the cyan monochromatic light with a yellow monochromatic light (usually of 570 nm).

The principle of the color match remains the basis of the modern anomaloscope, recognized as the best method to provide an accurate ability to categorize the congenital and acquired color vision dysfunctions in individuals. However, the anomaloscope is rarely used in clinical practice. The psycho-physical procedure using the anomaloscope is relatively long. The clinician needs some expertise to be able to compile and understand the test results. While some anomaloscopes are equipped with automated testing system, their prices remain relatively high.

There are several tests that practitioners prefer to employ to evaluate a patient's color vision. These tests are not expensive, are easy to use and the result are quick to execute. The most popular clinical tests are the pseudo isochromatic plates representing charts, printed with dots of various colors, arranged in a way that the dots of the same color form geometric figures (i.e. numbers, circles, cross or triangles) in contrast with the background image designed by dots of a different color. A clinical test may contain several charts with different colored symbols, in which the symbol color and the background color are not noticeable for some subjects with color vision perceptual abnormalities.

The most recent developments in the field of clinical examinations for the colors vision deficiency offer tests on the same principle as the pseudo isochromatic plates presented on the computer screen. There are several benefits to present colors vision tests on a computer screen:

Firstly, the test presentation and results can be automatized. Secondly, the colors can be presented in constant evolution, which increases the ability of the test to identify people with a mild form of the colors vision deficiency.

However, the use of a current computer screen to simulate tests for the color vision evaluation is limited for the tests procedures like the isochromatic plates. On the other hand, the clinical tests have a limited capacity relatively to the color match method in characterizing and quantifying deficiencies in individual color vision.

The anomaloscope remains the benchmark instrument used to evaluate the human color vision performances. So, there is a great interest in developing this procedure and in making it accessible through the modern technologies that generate colors, such as for example on a digital screen.

However, the anomaloscope method cannot be simulated on a standard RGB screen display because the standard RGB computer screen uses only the three main colors red, green and blue generated by lights having with relatively wide spectral band. All other colors, inclusively yellow, are generated from mixtures of the three primary colors. Several manufacturers offer digital screens with four or five primary colors, for example red, yellow, green, cyan and blue, to generate a large color gamut at a relatively higher luminance than when using traditional RGB displays. The four or five primary colors of these digital screens are generated by lights having relatively wide spectrum band. Consequently, the colors generated by the available multi-primary digital screens are still not optimal to simulate the anomaloscope method.

SUMMARY

According to the present disclosure, there is provided an anomaloscope comprising a display and a controller of the display. The display has pixels arranged in a plurality of groups, each group containing at least three pixels, each pixel being capable of emitting monochromatic light at a distinct wavelength. The controller of the display is operatively connected to the display. The controller of the display is configured to cause the display to emit, from at least one of the plurality of groups, light at a first one of the distinct wavelengths, to cause the display to emit, from at least another one of the plurality of groups, light mixtures at two other ones of the distinct wavelengths and to control intensities of the light emitted at each of the distinct wavelengths to generate of a pair of metameric colors between the light emitted at the first one of the distinct wavelengths and a mixture of the light emitted at the two other ones of the distinct wavelengths.

According to the present disclosure, there is also provided a method of generating pair of metameric colors. A display having pixels arranged in a plurality of groups is provided, each group containing at least three pixels, each pixel being capable of emitting monochromatic light at a distinct wavelength. Light is emitted, from at least one of the plurality of groups of the display, at a first one of the distinct wavelengths. Light is emitted, from at least another one of the plurality of groups of the display, at two other ones of the distinct wavelengths. Intensities of the light emitted by the display are controlled at each of the distinct wavelengths to generate the pair of metameric colors between the light emitted at the first one of the distinct wavelengths and a mixture of the light emitted at the two other ones of the distinct wavelengths.

The present disclosure further relates to a method of assessing an ability of a subject to discriminate between colors. A symbol is displayed on a display, the symbol having a first color, a background of the display having a second color, the first and second colors being metameric colors. One of the first and second colors is generated by the display using monochromatic light emitted at a first wavelength and another one of the first and second colors is generated by the display using monochromatic light emitted at second and third wavelengths. A controller provides a command to the display to control a level of contrast between the metameric colors. A response from the subject is received at the controller. The response identifies an aspect of the symbol. The controller evaluates the ability of the subject to discriminate between the first and second colors based on the received response.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which.

Like numerals represent like features on the various drawings.

DETAILED DESCRIPTION

Various aspects of the present disclosure generally address one or more of the problems related to the use of conventional colored displays in the generation of pairs of metameric colors. As expressed hereinabove, a standard RGB screen cannot generate pairs of metameric colors. Also, a conventional multi-primary color display having five primary colors can generate pairs of metameric colors, but these pairs of metameric colors are unsaturated.

The present technology introduces a display, with pixels that emit monochromatic light over at least three (3) distinct wavelengths to generate pairs of metameric colors. This display with monochromatic colors can simulate the color match method for color vision evaluation with similar performances of that of the conventional anomaloscopes.
Digital Colored Display to Simulate Rayleigh Color Match Procedure The Rayleigh color match procedure consists in evaluating a subject's ability to discriminate differences between two metameric colors, for example between yellow obtained from a mixture of red and green monochromatic lights (usually of 670 nm and respectively of 535 nm) and an actual yellow monochromatic light (of 589 nm) of variable intensity. In the context of the present disclosure, each monochromatic light forms a saturated color. Without limitation, a bandwidth each monochromatic light has a full width at half maximum (FWHM) of +/−10 nm.

A digital display with three types of pixels which emit monochromatic red, yellow and green (RYG) light is useful to generate pairs of metameric colors that simulate the Rayleigh color matching method with improved performance. As a non-limitative example, the SMP4-SRGY LED from Bivar Inc. may be used to produce the digital display. A specification for this LED is available at www.bivarcom/portals/0/products/SMP4-RGY.pdf, the disclosure of which is incorporated by reference herein.

Figure 1:
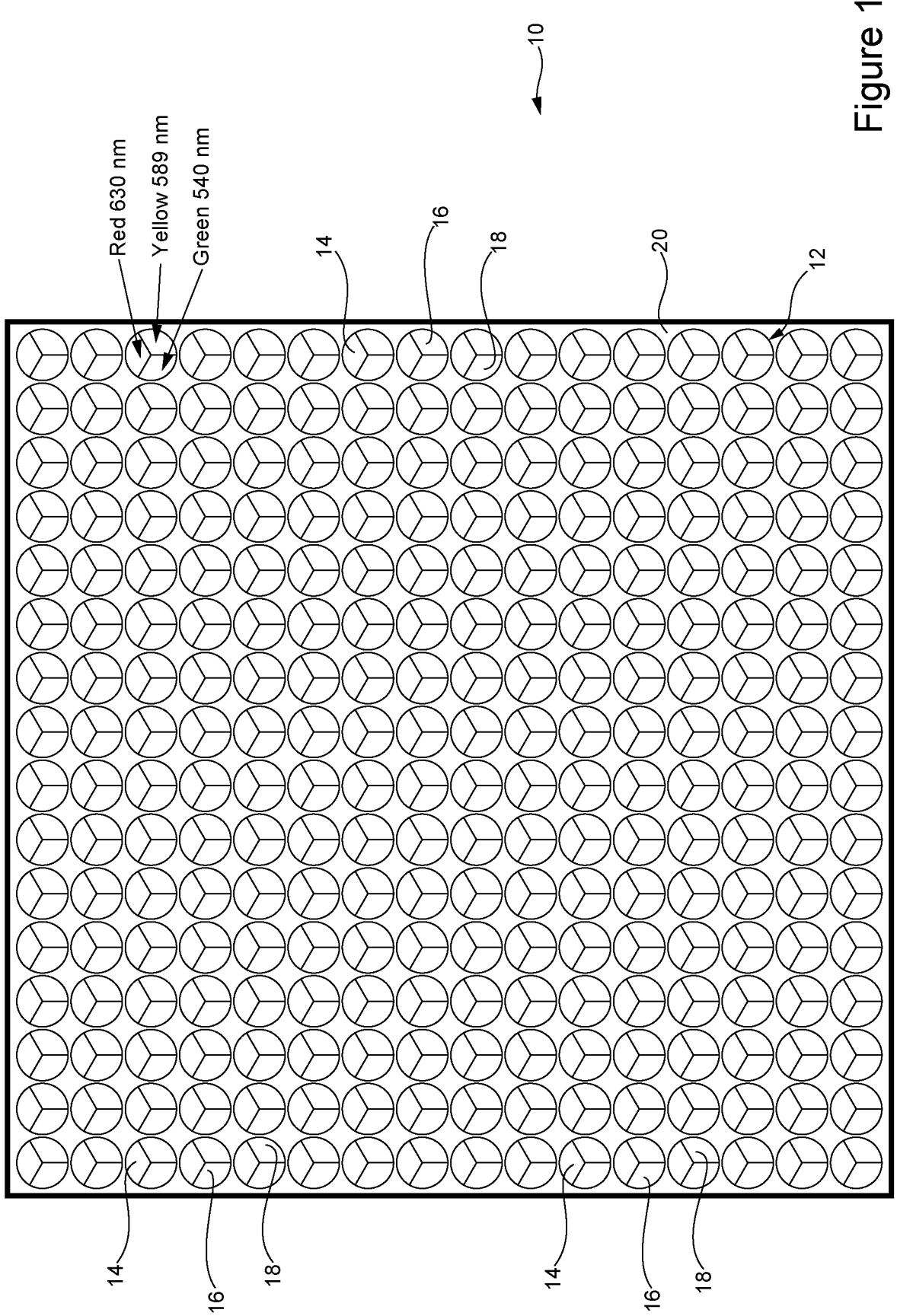
FIG. 1 is a highly schematic representation of a display having groups of pixels emitting monochromatic light at three (3) distinct wavelengths.

Referring now to the drawings, FIG. 1 is a highly schematic representation of a display having groups of pixels emitting monochromatic light at three (3) distinct wavelengths. An example of a display 10 may be represented by a matrix of 16 by 16 light emitting diodes (LED) 12, each LED 12 including one red pixel 14, one yellow pixel 16 and one green pixel 18. It should however be noted that, in a practical realization, the display 10 may include a much larger number of LEDs. A background 20 of the display 10 is normally very dark, being for instance black, but is shown as white on FIG. 1 for ease of illustration. In an embodiment, the pixels 14, 16 and 18 respectively generate monochromatic lights for red (630 nm), yellow (589 nm) and green (540 nm).

Figure 2:
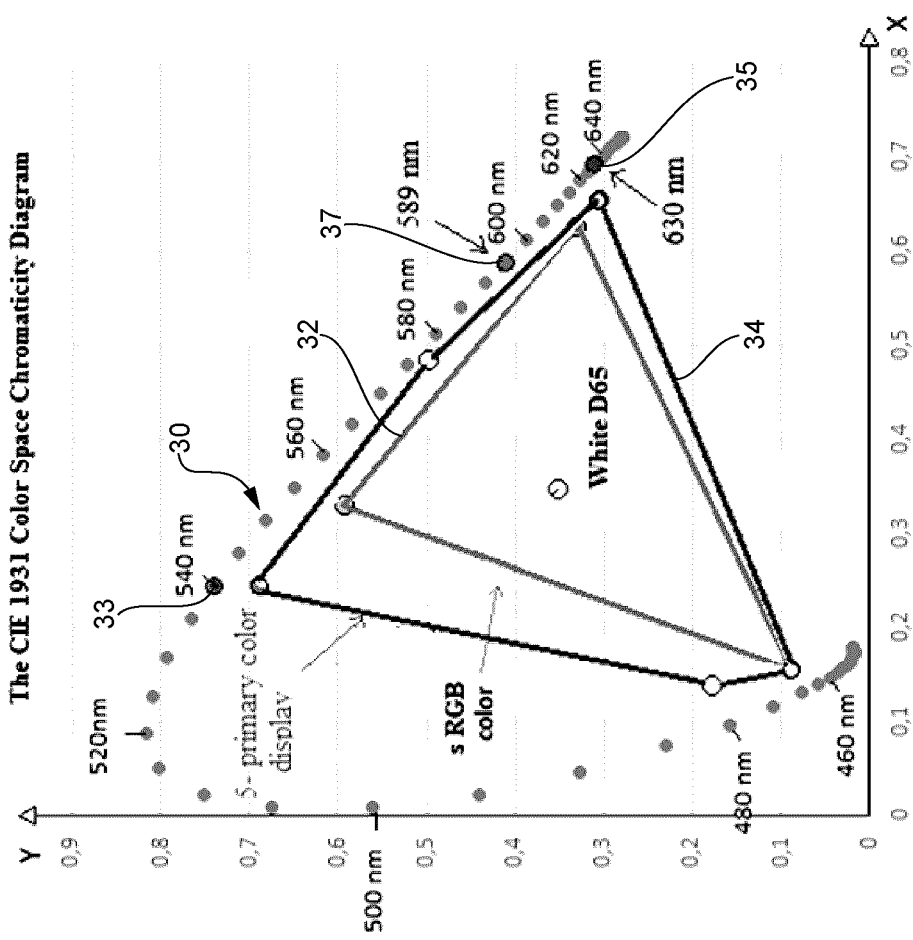
FIG. 2 illustrates on the CIE Chromaticity Diagram, the chromaticity of the three monochromatic lights of red (630 nm), green (540 nm) and yellow (589 nm) of a display which are compatible to simulate the Rayleigh color matching.

FIG. 2 illustrates on the CIE Chromaticity Diagram, the chromaticity of the three monochromatic lights of red (630 nm), green (540 nm) and yellow (589 nm) of a display which are compatible to simulate the Rayleigh color matching. The chromaticity of the primary colors for a standard RGB display and for a five primary colors of a multi-primary color display is also represented.

A chromaticity diagram 28 follows a CIE (International Commission on Illumination) 1931. The display 10 is compatible to simulate the Rayleigh color matching. The chromaticity 30 of the three pixels of the display 10 including green 33 (540 nm), red 35 (640 nm) and yellow 37 (589 nm) is shown on FIG. 2. The diagram also shows the chromaticity 32 of three primary colors of a standard RGB display and the chromaticity 34 for the five primary colors of a multi-primary color display. FIG. 2 demonstrates that the three primary colors of a standard RGB display are incompatible to generate pairs of metameric colors. Furthermore, a five primary color display can generate pairs of metameric colors but these pairs of metameric colors are unsaturated.

The three monochromatic colors (RYG) of the display 10 are saturated and aligned on the red-green chromaticity line, which can allow generating pairs of saturated metameric colors. The intensity of each monochromatic light in each LED can be controlled by a computer system used as a controller of the display in order to generate symbols contours defined by a metameric contrast on the red-green chromaticity line.

A subject capacity to distinguish various geometric shapes, as circles, cross or triangles, generated by the yellow monochromatic light in contrast with the background, which is a metameric yellow from a red-green mixture, can be evaluated using the display 10.

The colors vision evaluation on the display 10 with (RYG) monochromatic colors is comparable to the color vision evaluation that may be obtained using a Rayleigh anomaloscope. Tests used in evaluating a subject's color vision on the display 10 can be automatized. There is a large possibility to adapt the psycho-physical test procedure in relation with the age and the other specific test conditions. The display 10 can be controlled to finely adapt a contrast of the metameric colors, which increases the test accuracy.

Figure 3:
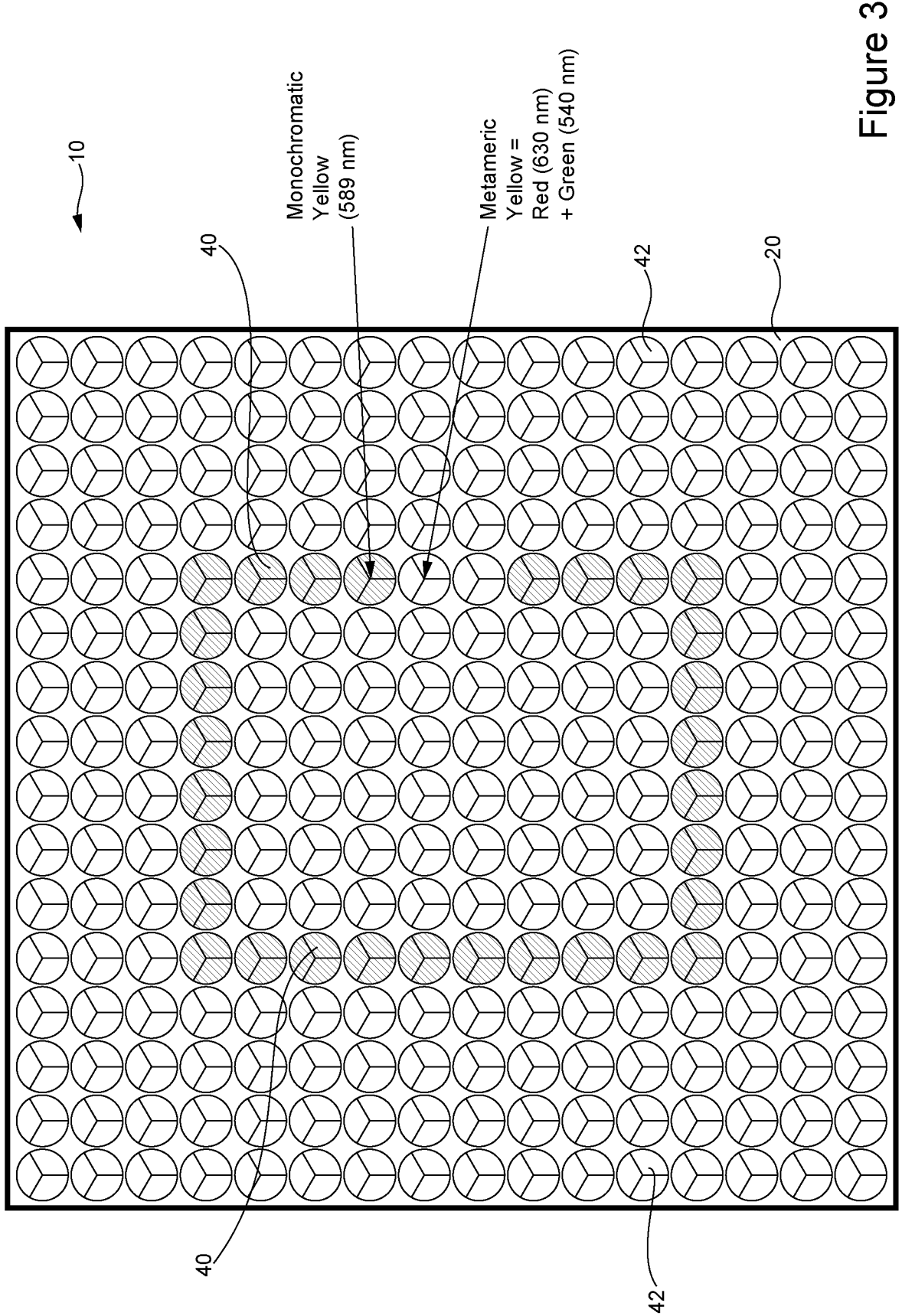
FIG. 3 shows a Landolt C optotype with metameric contrast generated on the display of FIG. 1.

A typical example for a stimulus test and procedure is illustrated by reference to FIG. 3, which shows a Landolt C optotype with metameric contrast generated on the display of FIG. 1. On the display 10, a portion 40 of the groups of pixels emits yellow monochromatic light. Another portion 42 of the groups of pixels emits metameric yellow generated from a combination of monochromatic red and green lights. The portion 40 forms a Landolt C optotype and the portion 42 form a background for the Landolt C optotype. An orientation of the C optotype on the display 10 may be presented randomly. In the course of an evaluation, the subject provides a response indicating his/her perception of the C optotype orientation for various intensities of the yellow monochromatic light that defines the C optotype and the different mixtures of the red-green light that define the display background colors. A controller for the display establishes the red-green mixtures of the background and the corresponding intensities of the yellow monochromatic light that define the C optotype, so that the optotype C is not noticeable for the subject.

A level of color contrast and/or intensity contrast may be controlled by an operator to better assess the color detection ability of a subject. On FIG. 3, a contrast between the portions 40 and 42 is exaggerated for ease of illustration.

Digital Colored Display to Simulate Moreland Color Match Procedure

The Moreland color match procedure is useful in evaluating the integrity of the blue color mechanism of a subject. Moreland has proposed to match a cyan monochromatic light (usually of 470 nm) with a mixture between blue and green monochromatic lights (usually of 440 nm and respectively of 488 nm). The cyan monochromatic light appears saturated relatively to all the blue and green lights mixtures and, for that reason, the cyan monochromatic light is mixed with a predetermined quantity of yellow monochromatic light (usually of 590 nm). Then, a simple digital display able to simulate the Moreland color match procedure may be represented by a matrix of 16×16 LEDs, where each LED has the capacity to generate four monochromatic lights: green (488 nm), cyan (470 nm), blue (440 nm) and yellow (590 nm).

In performing a test based on the Moreland color match procedure, the individual lens and the macular pigment absorptions affect the matching-range contribution between the blue-green primary mixture and the corresponding cyan and yellow lights generating large variability in the normal matching-range contributions between the blue-green primary mixture and the corresponding cyan and yellow lights.

Figure 4:
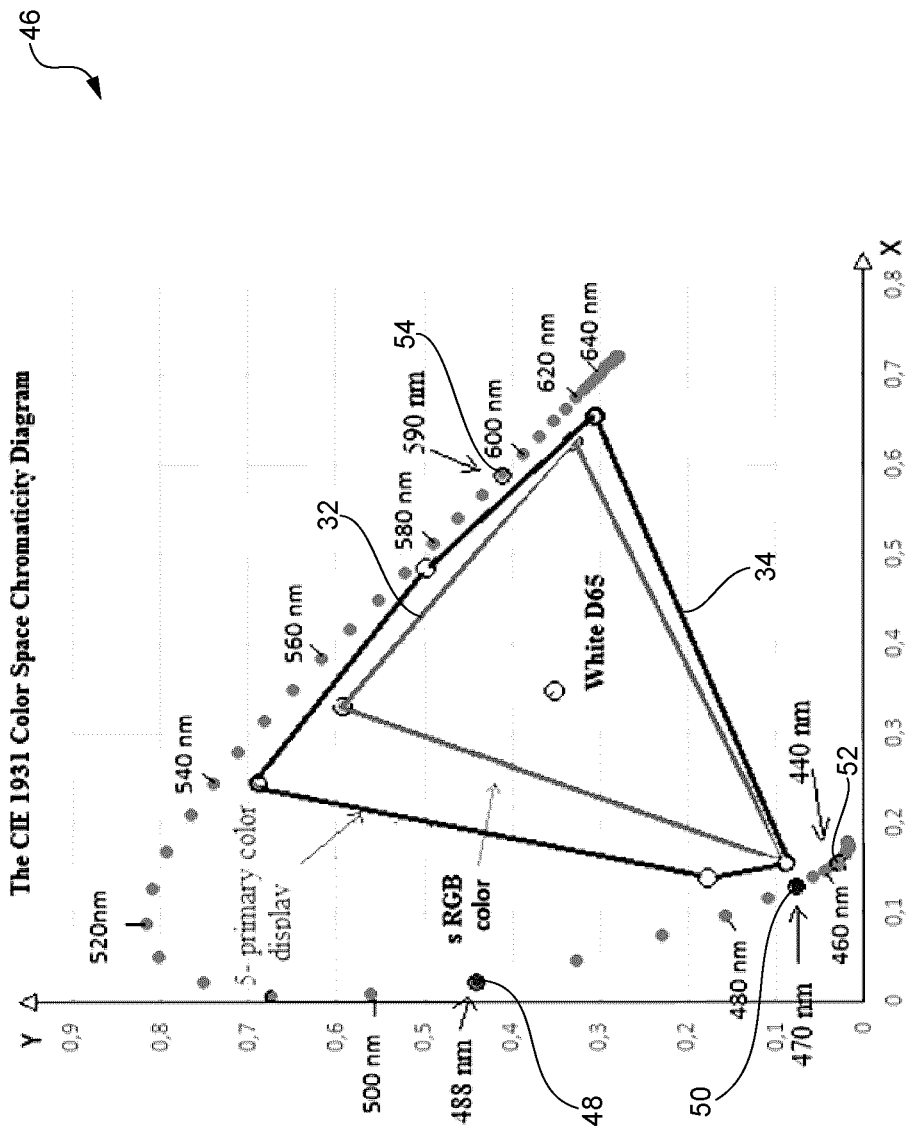
FIG. 4 illustrates the CIE Chromaticity Diagram with the chromaticity for the four monochromatic lights, green (488 nm), cyan (470 nm), blue (440 nm) and yellow (590 nm) of a display, which are compatible to simulate the Moreland color matching.

FIG. 4 illustrates the CIE Chromaticity Diagram with the chromaticity for the four monochromatic lights, green (488 nm), cyan (470 nm), blue (440 nm) and yellow (590 nm) of a display, which are compatible to simulate the Moreland color matching. A chromaticity diagram 46 also follows the CIE 1931 Color Space specification. The chromaticity 32 of three main colors of a standard RGB display and the chromaticity 34 for the five primary colors of a multi-primary color display are reproduced. The chromaticity for the four monochromatic lights able to simulate the Moreland color matching, including green 48 (488 nm), cyan 50 (470 nm), blue 52 (440 nm) and yellow 54 (590 nm), is also shown. The chromaticity of the primary colors for a standard RGB display and for a five primary colors of a multi-primary color display is also represented.

Figure 5:
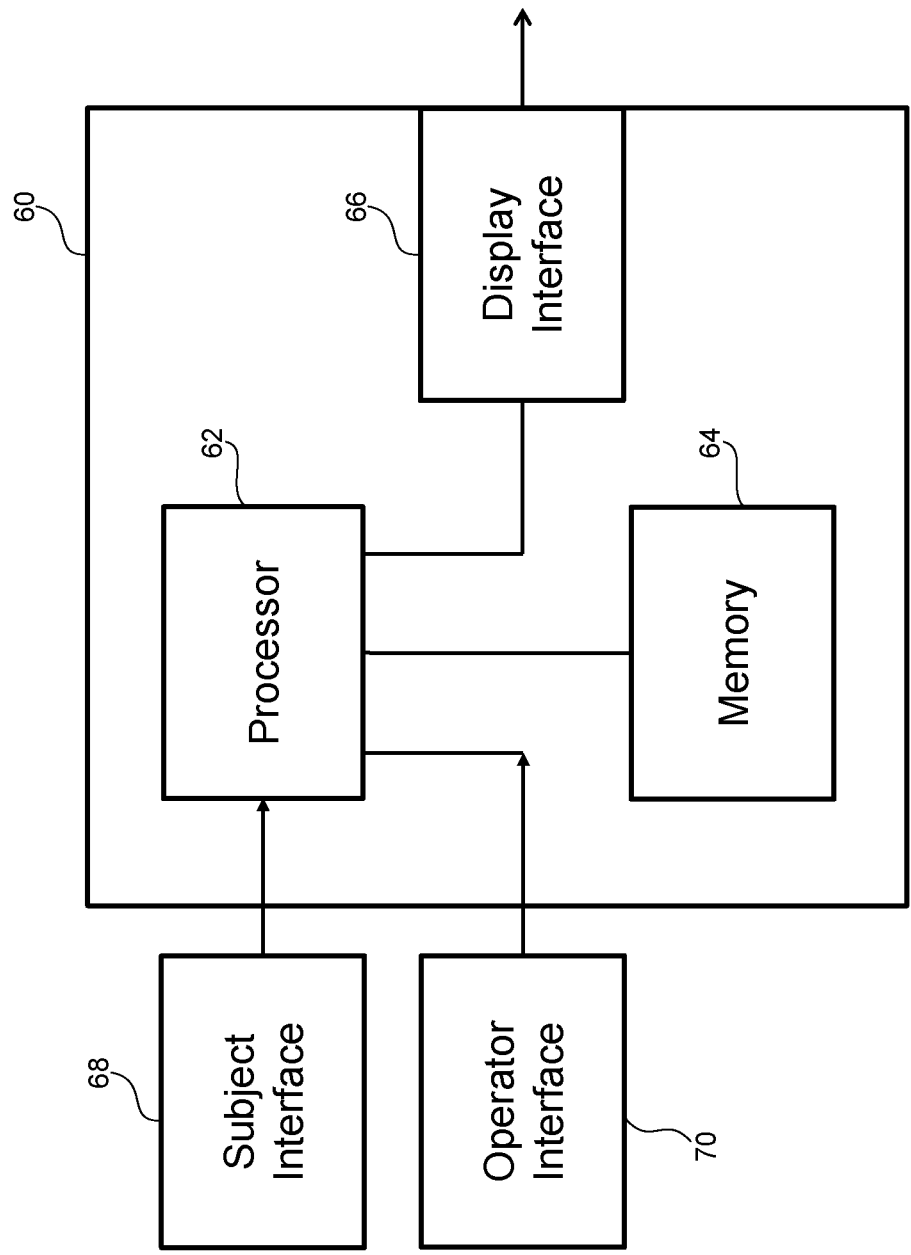
FIG. 5 is a block diagram of a controller of the display of FIG. 1.

FIG. 5 is a block diagram of a controller of the display of FIG. 1. A controller 60 comprises one or more processors 62 (without limitation, one processor 62 is shown to simplify the illustration), a memory 64 (without limitation, the memory 64 may include one or more memory devices), and a display interface 66. The controller 60 is connected to and receives commands from a subject interface 68 and an operator interface 70. The processor 62 controls the display 10 via the display interface 66 to cause the display 10 to emit, from at least one of the plurality of groups (i.e. at least one LED 12), light at a first one of the distinct wavelengths, to cause the display 10 to emit, from at least another one of the plurality of groups (i.e. at least another one LED 12), light at two other ones of the distinct wavelengths, and control intensities of the light emitted at each of the distinct wavelengths to generate a pair of metameric colors between the light emitted at the first one of the distinct wavelengths and a combination of the light emitted at the two other ones of the distinct wavelengths.

The operator interface 70 provides commands to the processor 62 to indicate which groups will emit light at the first one of the distinct wavelengths and which other groups will emit light at the two other ones of the distinct wavelengths. The operator 70 may for example select groups of a matrix defined on the display 10 to form a symbol. Other commands from the operator interface 70 may control a color contrast and/or an intensity contrast of the metameric colors.

During an evaluation, the subject uses the subject interface 68 to provide responses identifying a symbol, for instance an optotype, a letter, a number, an icon, or a geometric figure, being displayed on the display 10. The processor 62 evaluates an ability of the subject to discriminate between the first and second colors based on the received responses.

The anomaloscope including the display 10 and the controller 60 may be used to simulate the color matching procedures for color vision investigation in human subjects, for example in clinical optometry to detect and quantify a genetic color vision deficiencies in a subject or in the medical field to detect changes in normal color vision of a subject in relation to age, state of health, intoxication, and the like. Further uses are possible generally in the fields of health investigation, vision research, psychology and neuropsychology.

Figure 6:
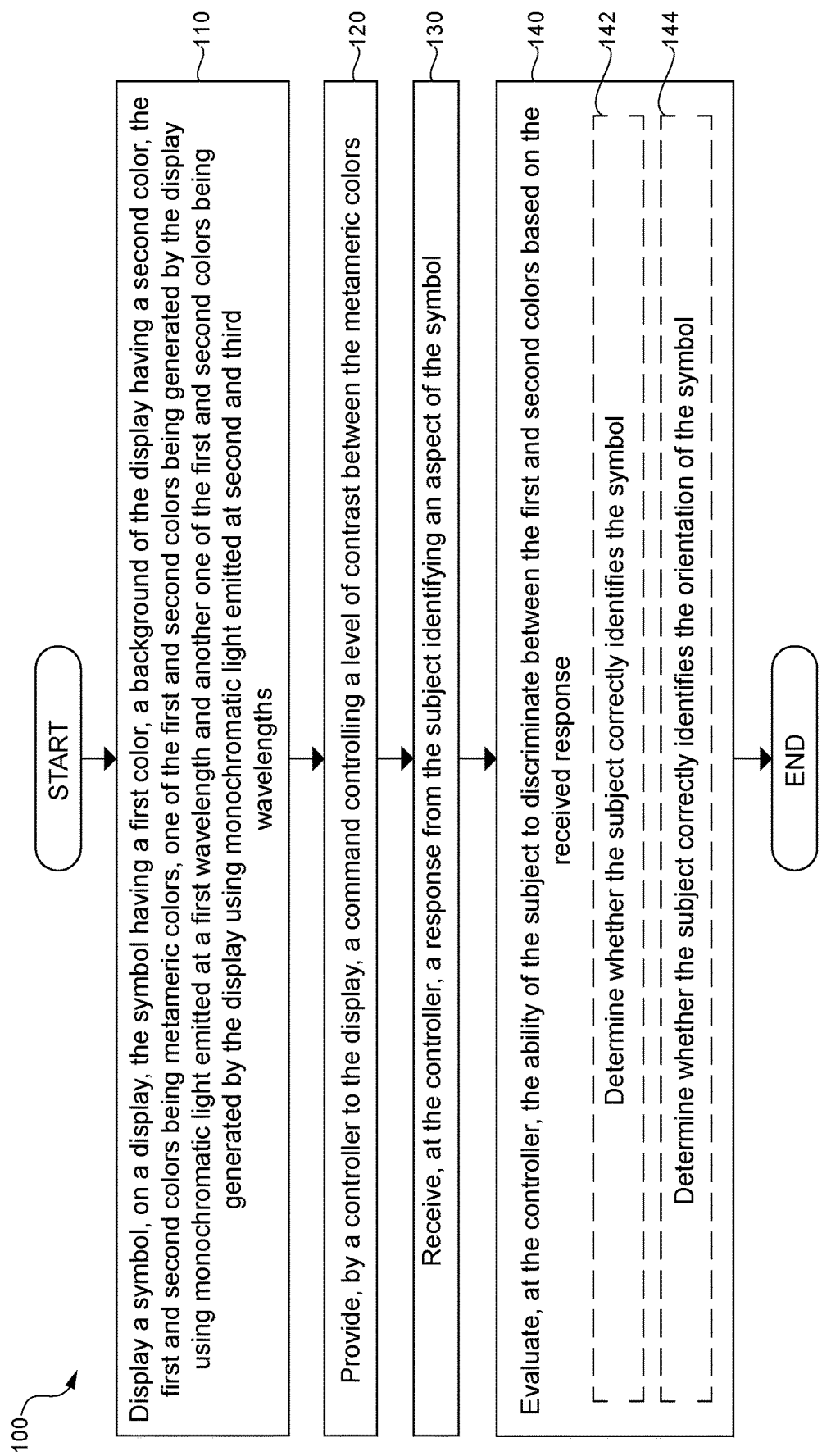
FIG. 6 is a flow chart of a method of assessing an ability of a subject to discriminate between colors.

FIG. 6 is a flow chart of a method of assessing an ability of a subject to discriminate between colors. On FIG. 6, a sequence 100 comprises a plurality of operations that may be executed in variable order, some of the operations possibly being executed concurrently, some of the operations being optional. The sequence starts with operation 110 comprising displaying a symbol, on a display, the symbol having a first color, a background of the display having a second color, the first and second colors being metameric colors, one of the first and second colors being generated by the display using monochromatic light emitted at a first wavelength and another one of the first and second colors being generated by the display using monochromatic light emitted at second and third wavelengths. Without limitation, the symbol may be an optotype, a letter, a number, an icon, or a geometric figure. A controller provides to the display, at operation 120, a command controlling a level of contrast between the metameric colors. The contrast between the metameric colors may comprise a color contrast, an intensity contrast, or both. The controller receives, at operation 130, a response from the subject identifying an aspect of the symbol. Then at operation 140, the controller evaluates the ability of the subject to discriminate between the first and second colors based on the received response. In a variant, operation 140 comprises sub-operation 142 in which the controller determines whether the subject correctly identifies the symbol. In the same or another variant, operation 140 comprises sub-operation 144 in which the controller determines the subject correctly identifies the orientation of the symbol Each of the operations shown on FIG. 6 may be configured to be processed by one or more processors, the one or more processors being coupled to a memory.

Those of ordinary skill in the art will realize that the description of the anomaloscope, of the method of generating pairs of metameric colors, and of the method of assessing an ability of a subject to discriminate between colors are illustrative only and are not intended to be in any way limiting. Other embodiments will readily suggest themselves to such persons with ordinary skill in the art having the benefit of the present disclosure. Furthermore, the disclosed anomaloscope and methods may be customized to offer valuable solutions to existing needs and problems related the use of conventional RGB displays in the generation of pairs of metameric colors. In the interest of clarity, not all of the routine features of the implementations of the anomaloscope and of the methods are shown and described. In particular, combinations of features are not limited to those presented in the foregoing description as combinations of elements listed in the appended claims form an integral part of the present disclosure. It will, of course, be appreciated that in the development of any such actual implementation of the anomaloscope and methods, numerous implementation-specific decisions may need to be made in order to achieve the developer's specific goals, such as compliance with application-, system-, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the fields of optometry and ophthalmology having the benefit of the present disclosure.

In accordance with the present disclosure, the components, process operations, and/or data structures described herein may be implemented using various types of operating systems, computing platforms, network devices, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used. Where a method comprising a series of operations is implemented by a computer, a processor operatively connected to a memory, or a machine, those operations may be stored as a series of instructions readable by the machine, processor or computer, and may be stored on a non-transitory, tangible medium.

Systems and modules described herein may comprise software, firmware, hardware, or any combination(s) of software, firmware, or hardware suitable for the purposes described herein. Software and other modules may be executed by a processor and reside on a memory of servers, workstations, personal computers, computerized tablets, personal digital assistants (PDA), and other devices suitable for the purposes described herein. Software and other modules may be accessible via local memory, via a network, via a browser or other application or via other means suitable for the purposes described herein. Data structures described herein may comprise computer files, variables, programming arrays, programming structures, or any electronic information storage schemes or methods, or any combinations thereof, suitable for the purposes described herein.

The present disclosure has been described in the foregoing specification by means of non-restrictive illustrative embodiments provided as examples. These illustrative embodiments may be modified at will. The scope of the claims should not be limited by the embodiments set forth in the examples, but should be given the broadest interpretation consistent with the description as a whole.

What is claimed is:

1. An anomaloscope, comprising:
a display having pixels arranged in a plurality of groups, each group containing at least three pixels, each pixel being capable of emitting monochromatic light at a distinct wavelength; and
a controller of the display operatively connected to the display and configured to:
cause the display to emit, from at least one of the plurality of groups, light at a first one of the distinct wavelengths;
cause the display to emit, from at least another one of the plurality of groups, light at two other ones of the distinct wavelengths; and
control intensities of the light emitted at each of the distinct wavelengths to generate of a pair of metameric colors between the light emitted at the first one of the distinct wavelengths and a combination of the light emitted at the two other ones of the distinct wavelengths.

2. The anomaloscope of claim 1, further comprising an operator interface operatively connected to the controller of the display and configured to provide to the controller of the display an indication of the groups emitting light at the first one of the distinct wavelengths.

3. The anomaloscope of claim 2, wherein the operator interface is further configured to control a level of contrast between the metameric colors.

4. The anomaloscope of claim 3, wherein the contrast between the metameric colors is selected from a color contrast, an intensity contrast and a combination thereof.

5. The anomaloscope of claim 2, wherein the indication of the groups emitting light at the first one of the distinct wavelengths causes the display to show a symbol.

6. The anomaloscope of claim 5, wherein:
the plurality of groups of pixels form a matrix on the display; and
the indication of the groups emitting light at the first one of the distinct wavelengths comprises a mapping of the symbol on the matrix.

7. The anomaloscope of claim 5, wherein the symbol is selected from an optotype, a letter, a number, an icon, and a geometric figure.

8. The anomaloscope of claim 5, wherein the controller of the display is adapted to control an orientation of the symbol on the display.

9. The anomaloscope of claim 1, wherein each group comprises a red pixel, a green pixel and a yellow pixel.

10. The anomaloscope of claim 9, wherein:
red pixels are adapted to emit light at 630 nanometers (nm);
green pixels are adapted to emit light at 540 nanometers (nm); and
yellow pixels are adapted to emit light at 589 nanometers (nm).

11. The anomaloscope of claim 9, wherein:
the yellow pixels emit the light at the first one of the distinct wavelengths; and
the red and green pixels emit the light at the two other ones of the distinct wavelengths.

12. The anomaloscope of claim 1, wherein each group comprises a green pixel, a cyan pixel, a blue pixel and a yellow pixel.

13. The anomaloscope of claim 12, wherein:
green pixels are adapted to emit light at 488 nanometers (nm);
cyan pixels are adapted to emit light at 470 nanometers (nm);
blue pixels are adapted to emit light at 440 nanometers (nm); and
yellow pixels are adapted to emit light at 590 nanometers (nm).

14. The anomaloscope of claim 12, wherein:
the yellow pixels emit the light at the first one of the distinct wavelengths;
the blue and green pixels emit the light at the two other ones of the distinct wavelengths;
the cyan pixels emit light at a fourth distinct wavelength, the first one of the distinct wavelengths being combined the fourth wavelength.

15. The anomaloscope of claim 1, wherein the controller of the display comprises a processor operatively connected to a memory.

16. The anomaloscope of claim 15, wherein the memory comprises a non-transitory storage medium storing instructions that, when executed by the processor, cause the controller of the display to control the display.

17. A method of generating pairs of metameric colors, comprising:
providing a display having pixels arranged in a plurality of groups, each group containing at least three pixels, each pixel being capable of emitting monochromatic light at a distinct wavelength;
emitting, from at least one of the plurality of groups of the display, light at a first one of the distinct wavelengths;
emitting, from at least another one of the plurality of groups of the display, light at two other ones of the distinct wavelengths; and
controlling intensities of the light emitted by the display at each of the distinct wavelengths to generate pairs of metameric colors between the light emitted at the first one of the distinct wavelengths and a combination of the light emitted at the two other ones of the distinct wavelengths.

18. A method of assessing an ability of a subject to discriminate between colors, comprising:
displaying a symbol, on a display, the symbol having a first color, a background of the display having a second color, the first and second colors being metameric colors, one of the first and second colors being generated by the display using monochromatic light emitted at a first wavelength and another one of the first and second colors being generated by the display using monochromatic light emitted at second and third wavelengths;
providing, by a controller to the display, a command controlling a level of contrast between the metameric colors;
receiving, at the controller, a response from the subject identifying an aspect of the symbol; and
evaluating, at the controller, the ability of the subject to discriminate between the first and second colors based on the received response.

19. The method of claim 18, wherein the contrast between the metameric colors is selected from a color contrast, an intensity contrast and a combination thereof.

20. The method of claim 18, wherein the symbol is selected from an optotype, a letter, a number, an icon, and a geometric figure.

21. The method of claim 18, wherein evaluating, at the controller, the ability of the subject to discriminate between the first and second colors comprises determining whether the subject correctly identifies the symbol.

22. The method of claim 18, wherein the controller of the display is adapted to control an orientation of the symbol on the display.

23. The method of claim 22, wherein evaluating, at the controller, the ability of the subject to discriminate between the first and second colors comprises determining whether the subject correctly identifies the orientation of the symbol.

24. The method of claim 18, wherein:
the first wavelength is 630 nanometers (nm);
the second wavelength 540 nanometers (nm); and
the third wavelength 589 nanometers (nm).

25. The method of claim 18, wherein:
the first wavelength is 488 nanometers (nm);
the second wavelength is 470 nanometers (nm);
the third wavelength is 589 nanometers (nm); and
the display further emits light at a fourth wavelength, the fourth wavelength being 590 nanometers (nm), the first wavelength being combined the fourth wavelength.

\* \* \* \* \*